United States Patent
Gallagher et al.

(10) Patent No.: US 10,494,347 B2
(45) Date of Patent: *Dec. 3, 2019

(54) PROCESSES FOR THE PREPARATION OF URACIL DERIVATIVES

(71) Applicant: Neurocrine Biosciences, Inc., San Diego, CA (US)

(72) Inventors: Donald J. Gallagher, Hopkinton, MA (US); Laszlo R. Treiber, San Diego, CA (US); Robert Michael Hughes, San Diego, CA (US); Onorato Campopiano, Hayward, CA (US); Peng Wang, Carlsbad, CA (US); Yuxin Zhao, San Diego, CA (US); Shine K. Chou, Wildwood, MO (US); Michael Allen Ouellette, San Diego, CA (US); Donald Nicholas Hettinger, Broomfield, CO (US)

(73) Assignee: Neurocrine Biosciences, Inc., San Deigo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/833,513

(22) Filed: Dec. 6, 2017

(65) Prior Publication Data

US 2018/0346428 A1 Dec. 6, 2018

Related U.S. Application Data

(60) Continuation of application No. 15/406,476, filed on Jan. 13, 2017, now Pat. No. 9,868,706, which is a continuation of application No. 15/174,774, filed on Jun. 6, 2016, now abandoned, which is a continuation of application No. 14/309,732, filed on Jun. 19, 2014, now Pat. No. 9,382,214, which is a division of application No. 12/741,819, filed as application No. PCT/US2008/082873 on Nov. 7, 2008, now Pat. No. 8,765,948.

(60) Provisional application No. 60/986,227, filed on Nov. 7, 2007.

(51) Int. Cl.
| | | |
|---|---|---|
| *C07D 239/54* | (2006.01) | |
| *C07D 239/553* | (2006.01) | |
| *A61P 15/00* | (2006.01) | |
| *A61K 9/14* | (2006.01) | |
| *A61K 9/16* | (2006.01) | |

(52) U.S. Cl.
CPC ............ *C07D 239/54* (2013.01); *A61P 15/00* (2018.01); *C07D 239/553* (2013.01); *A61K 9/146* (2013.01); *A61K 9/1688* (2013.01)

(58) Field of Classification Search
CPC . C07D 239/02; C07D 239/54; C07D 239/553
See application file for complete search history.

(56) References Cited

U.S. PATENT DOCUMENTS

| | | | |
|---|---|---|---|
| 6,608,197 B2 | 8/2003 | Zhu | |
| 6,872,728 B2 | 3/2005 | Zhu | |
| 7,015,226 B2 | 3/2006 | Huang | |
| 7,056,927 B2 | 6/2006 | Guo | |
| 7,071,200 B2 | 7/2006 | Zhu | |
| 7,176,211 B2 | 2/2007 | Guo | |
| 7,179,815 B2 | 2/2007 | Zhu | |
| 7,229,995 B2 | 6/2007 | Huang | |
| 7,419,983 B2 | 9/2008 | Guo | |
| 7,462,625 B2 | 12/2008 | Zhu | |
| 7,501,429 B2 | 3/2009 | Weaver | |
| 8,765,948 B2 * | 7/2014 | Gallagher | C07D 239/553 544/311 |
| 9,382,214 B2 * | 7/2016 | Gallagher | C07D 239/553 |
| 9,868,706 B2 * | 1/2018 | Gallagher | C07D 239/553 |

FOREIGN PATENT DOCUMENTS

| | | |
|---|---|---|
| WO | 2005007164 | 1/2005 |
| WO | 2007122634 | 11/2007 |
| WO | 2017221144 | 12/2017 |
| WO | 2018189213 | 10/2018 |

OTHER PUBLICATIONS

Chen, C. et al., "Discovery of sodium R-(+)-4-{2-[5-(2-fluoro-3-methoxyphenyl)-3-(2-fluoro-6-[trifluoromethyl] benzyl)-4-methyl-2,6-dioxo-3,6-dihydro-2H-pyrimidin-1-yl]-1-phenylethylamino}butyrate (elagolix), a potent and orally available nonpeptide antagonist of the human gonadotropin-releasing hormone receptor", J Med Chem., 51 (23):7478-85, (2008).
U.S. Appl. No. 16/020,814; Non-Final Office Action, dated Apr. 1, 2019; 6 pages.
Database Registry (online), Chemical Abstract Service, Columbus, Ohio, U.S.; Mar. 20, 2003, XPO02515863, retrieved from STN, Database accession No. 500114-68-1, compound m 500114-68-1, abstract.
Database Registry (online), Chemical Abstract Service, Columbus, Ohio, U.S.; Mar. 20, 2003, XPO02515864, retrieved from STN, Database accession No. 2008: 10329, compound m 500114-64-7, abstract.
Felberbaum et al., "Clinical application of GnRH-antagonists," Molecular and Cellular Endocrinolozv 166:9-14, 2000.
U.S. Appl. No. 15/174,774; Application as filed, dated Jun. 6, 2016, 32 pages.

(Continued)

Primary Examiner — Alexander R Pagano
Assistant Examiner — Ebenezer O Sackey
(74) Attorney, Agent, or Firm — Lauren L. Stevens

(57) ABSTRACT

The present invention relates to processes and intermediates for preparing Gonadotropin-Releasing Hormone (GnRH) receptor antagonists of structure (VI); and stereoisomers and pharmaceutically acceptable salts thereof.

8 Claims, No Drawings

(56) References Cited

OTHER PUBLICATIONS

U.S. Appl. No. 16/020,814; Application as filed, dated Jun. 27, 2018, pages.

Western, E. et al., "Efficient One-Step Suzuki Arylation of Unprotected Halonucleosides, Using Water-Soluble Palladium Catalysts", J Org Chem., 68(17):6767-74, (2003).

Xia et al., "Microwave-assisted rapid synthesis of 5-iodouracil derivatives," Huaxue Shiji 29(12):756-758, 2007. (English translation unavailable).

* cited by examiner

PROCESSES FOR THE PREPARATION OF URACIL DERIVATIVES

FIELD OF THE INVENTION

The present invention relates to processes for the preparation of uracil derivatives which may be useful as gonadotropin-releasing hormone receptor antagonists.

BACKGROUND OF THE INVENTION

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-NH$_2$) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostate cancer, breast cancer, endometriosis, uterine leiomyoma (fibroids), ovarian cancer, prostatic hyperplasia, assisted reproductive therapy, and precocious puberty (*The Lancet* 358:1793-1803, 2001; *Mol. Cell. Endo.* 166:9-14, 2000). For example, peptidic GnRH agonists, such as leuprorelin (pGlu-His-Trp-Ser-Tyr-d-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2-3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

The present invention relates to synthetic routes to produce various uracil derivatives including the compounds 4-[[(1R)-2-[5-(2-fluoro-3-methoxyphenyl)-3-[[2-fluoro-6-(trifluoromethyl)phenyl]methyl]-3,6-dihydro-4-methyl-2,6-dioxo-1(2H)-pyrimidinyl]-1-phenylethyl]amino]-butanoic acid and its sodium and calcium salts, 4-[[(1R)-2-[5-(2-chloro-3-methoxyphenyl)-3-[[2-fluoro-6-(trifluoromethyl)phenyl]methyl]-3,6-dihydro-4-methyl-2,6-dioxo-1(2H)-pyrimidinyl]-1-phenylethyl]amino]-butanoic acid and its sodium and calcium salts, and 5-iodo-6-methyl-1-(2-methyl-6-trifluoromethyl-benzyl)-1H-pyrimidine-2,4-dione.

Uracil derivatives of formula (I) are described as GnRH antagonists in U.S. Pat. Nos. 6,608,197 and 6,872,728.

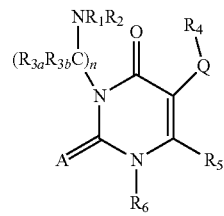

Additional uracil derivatives of formula (II) are described in U.S. Pat. No. 7,056,927.

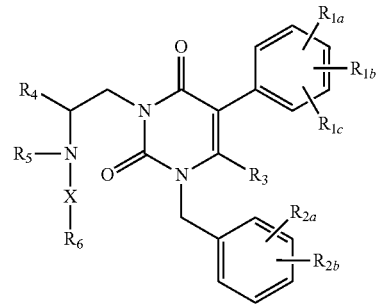

Additional uracil derivatives of formula (III) are described in U.S. Pat. No. 7,015,226.

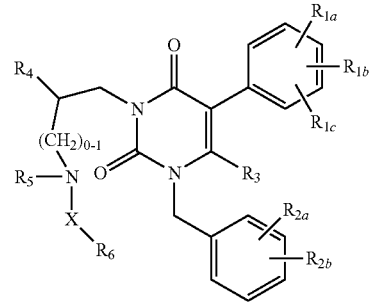

Additional uracil derivatives of formula (IV) are described in U.S. Pat. No. 7,071,200.

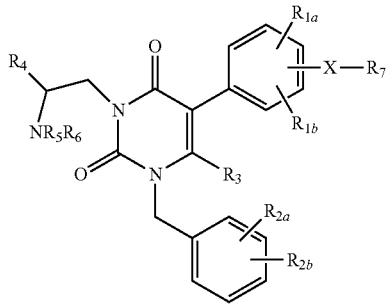

Additional uracil derivatives of formula (V) are described in WO2005007164.

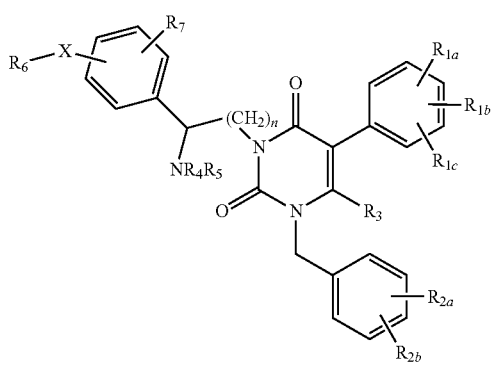

These patents and application are hereby incorporated by reference in their entirety.

SUMMARY OF THE INVENTION

The present invention provides methods amenable to large scale preparation of substituted uracil derivatives which are useful as GnRH antagonists. Included are intermediates such as 5-iodo substituted uracils and processes which are useful in preparing uracils of formulas (I) to (V).

DETAILED DESCRIPTION OF THE INVENTION

The present invention provides processes for preparing compounds of formula (VI):

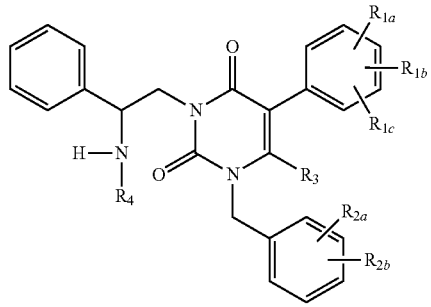

or a stereoisomer or pharmaceutically acceptable salt thereof,
wherein:
$R_{1a}$, $R_{1b}$ and $R_{1c}$ are the same or different and independently hydrogen, halogen, $C_{1-4}$alkyl, hydroxy or alkoxy;
$R_{2a}$ and $R_{2b}$ are the same or different and independently hydrogen, halogen, trifluoromethyl, cyano or —$SO_2CH_3$;
$R_3$ is hydrogen or methyl; and
$R_4$ is hydrogen, —$C_{1-6}$alkanediyl-COOH, or —C(=O)O-(t-butyl).

As used herein, the above terms have the following meaning:
"$C_{1-4}$alkyl" means a straight chain or branched, noncyclic or cyclic hydrocarbon containing from 1 to 4 carbon atoms. Representative straight chain alkyls include methyl, ethyl, n-propyl, n-butyl, and the like; branched alkyls include isopropyl, sec-butyl, isobutyl, tert-butyl, and the like; while cyclic alkyls include cyclopropyl and the like.

"$C_{1-6}$alkanediyl" means a divalent $C_{1-6}$alkyl from which two hydrogen atoms are taken from the same carbon atom or from different carbon atoms, such as —$CH_2$—, —$CH_2CH_2$—, —$CH_2CH_2CH_2$—, —$CH(CH_3)CH_2CH_2$—, —$CH_2C(CH_3)_2CH_2$—, and the like.

"Halogen" means fluoro, chloro, bromo or iodo, typically fluoro and chloro.

"Hydroxy" means —OH.

"Alkoxy" means —O—($C_{1-4}$alkyl).

"Cyano" means —CN.

In an embodiment, the compounds of formula (VI) may be prepared via intermediate (VII):

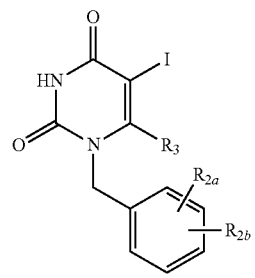

wherein $R_{2a}$, $R_{2b}$ and $R_3$ are as defined above.

In an embodiment, a compound of formula (VII) may be reacted with a compound of formula (VIII):

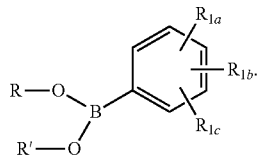

Where R is H or $C_{1-4}$alkyl, R' is H or $C_{1-4}$alkyl or R and R' taken together form $C_{1-6}$alkanediyl.

In an embodiment, the compounds of formula VI may be isolated as crystalline material, amorphous material, or a mixture of both. In an embodiment, amorphous material may be isolated by lyophilization, spray drying, co-spraying, precipitation or co-precipitation.

In general, the compounds of structure (VI) above may be made by the following reaction schemes, wherein all substituents are as defined above unless indicated otherwise.

Scheme 1

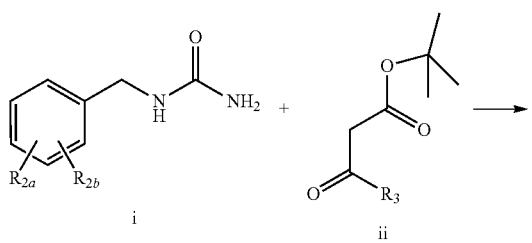

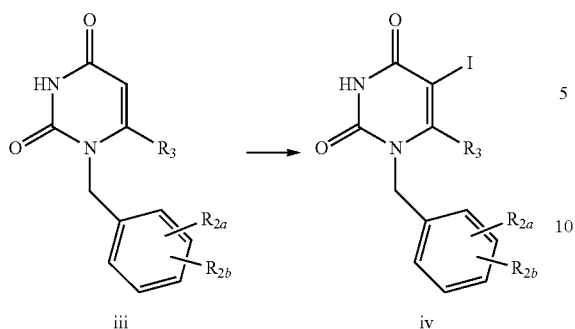

iii → iv

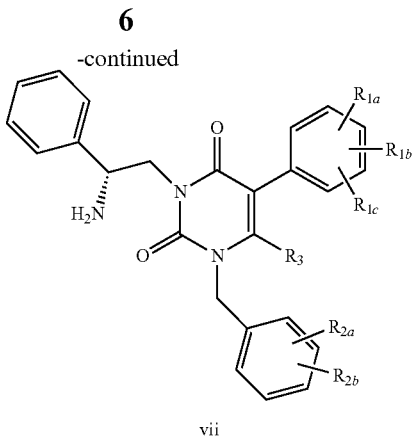

vii

Ureas i may be heated with various acetoacetates ii (such as t-butyl acetoacetate as shown) with removal of the generated alcohol to generate an acyclic intermediate which is cyclized to compound iii with an acid catalyst such as p-toluenesulfonic acid. The acetoacetate ii provides a procedure which is less hazardous than diketene. Reaction of iii with an iodinating reagent such as iodine monochloride results in compound iv in high yield.

Scheme 2

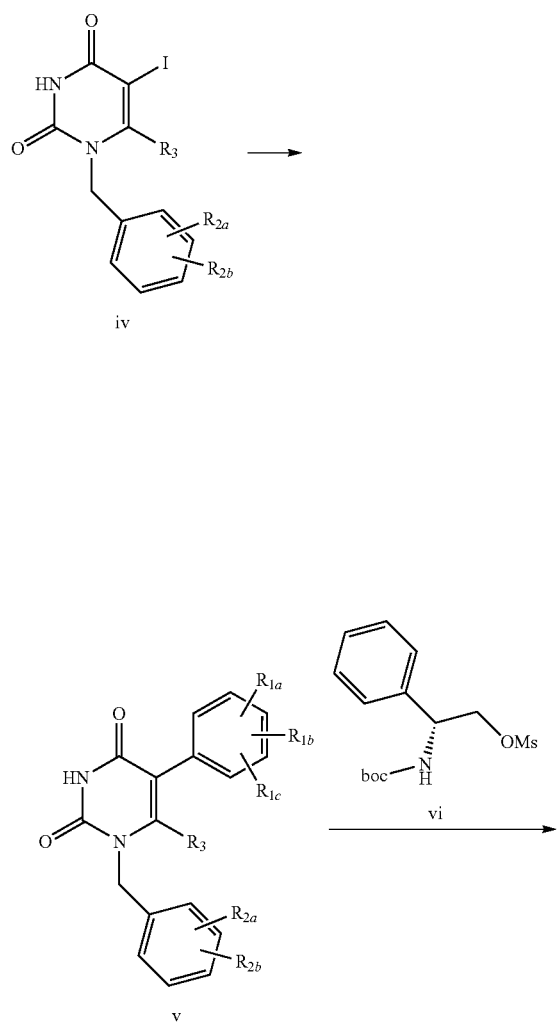

Compound iv is coupled with an appropriate boronic acid (such as 2-halo-3-methoxyphenyl boronic acid) or boronic acid ester under palladium catalysis conditions to generate v. Appropriate palladium sources include palladium acetate and tris(dibenzylidene-acetone)dipalladium(0) while tri-t-butylphosphine and tri-t-butylphosphonium tetrafluoroborate are acceptable phosphine ligands. Compound v and mesylate vi react in the presence of a base (such as potassium carbonate or potassium phosphate) to generate Boc-protected material which is deprotected under acidic conditions such as trifluoroacetic acid in methylene chloride or methanesulfonic acid in isopropyl acetate to yield compound vii.

Compounds of the present invention may exist as amorphous solids. An amorphous solid is generally defined as a non-crystalline solid in which molecules are not organized in a definite lattice. 4-((R)-2-[5-(2-Fluoro-3-methoxy-phenyl)-3-(2-fluoro-6-trifluoromethyl-benzyl)-4-methyl-2,6-di-oxo-3,6-dihydro-2H-pyrimidin-1-yl]-1-phenyl-ethyl-amino)-butyric acid sodium salt (compound 5-1) is an example of a compound of the present invention which may be isolated as an amorphous solid. Amorphous solids may be isolated from various procedures such as lyophilization, spray drying, co-spraying, precipitation or co-precipitation.

Compounds of the present invention, in particular compound 5-1, may be precipitated as amorphous solids. This precipitation may involve extraction of a compound of formula (VI), in particular compound 5-1, from an aqueous mixture into an organic solvent by adding an appropriate additive (such as sodium chloride, sodium acetate and sodium hydroxide) to the mixture. Appropriate organic solvents include methylisobutyl ketone, isopropylacetate and methylethyl ketone. The compound of interest may then be precipitated using an appropriate anti-solvent and isolated as an amorphous solid. Appropriate anti-solvents include nonpolar organic solvents such as heptane and hexanes.

These materials may be formulated as amorphous co-solutions where the co-solution may help stabilize the resulting amorphous solid.

Compounds of the present invention may be spray dried by itself or with other excipients such as PVP (polyvinyl pyrrolidone, Kollidon's), HPMC (hydroxypropylmethylcellulose), mannitol, or other suitable carrier.

These procedures may serve to stabilize amorphic material via solid solution formation with appropriate polymers (Kollidon, HPMC, etc.) resulting from evaporation or grinding techniques.

EXAMPLES

Analytical Methods:
HPLC Method 1:
Column: Zorbax SB-C18, 3.5μ, 3×150 mm
Mobile Phase A=0.1% trifluoroacetic acid in water
Mobile Phase B=0.1% trifluoroacetic acid in acetonitrile
Gradient Table (data collection stops at 13 min):

| Time | 0.1% TFA/H$_2$O | 0.1% TFA/CH$_3$CN | Flow Rate |
| --- | --- | --- | --- |
| 0 | 70 | 30 | 0.75 |
| 12.0 | 10 | 90 | 0.75 |
| 13.0 | 2.5 | 97.5 | 0.75 |
| 13.1 | 70 | 30 | 1.2 |
| 15.00 | 70 | 30 | 1.2 |
| 15.5 | 70 | 30 | 0.75 |

Injection Volume: 2.5 μL
Column Temperature: Controlled at 20° C.
UV Detection: 220 nm and 254 nm (220 nm data used for all analyses)
Diluent: 70:30 CH$_3$CN:H$_2$O

Example 1

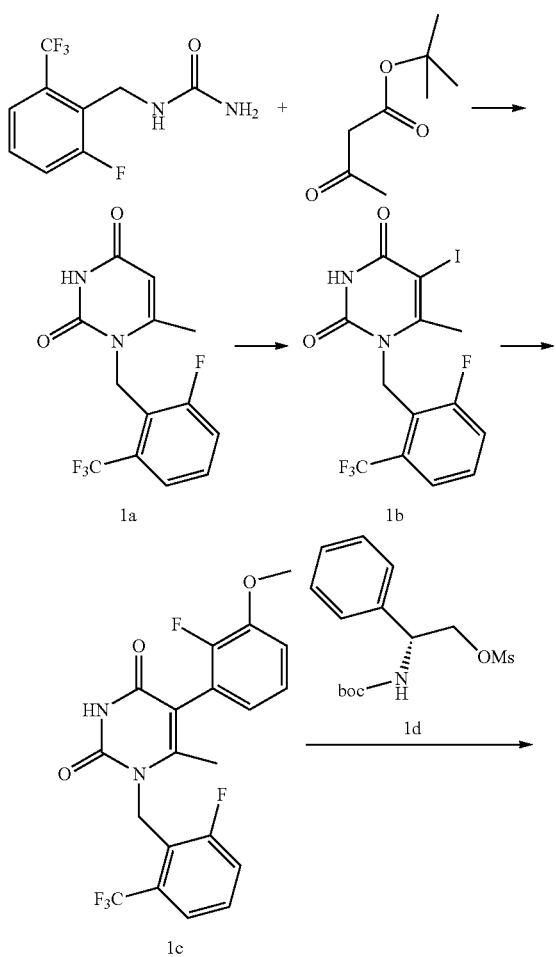

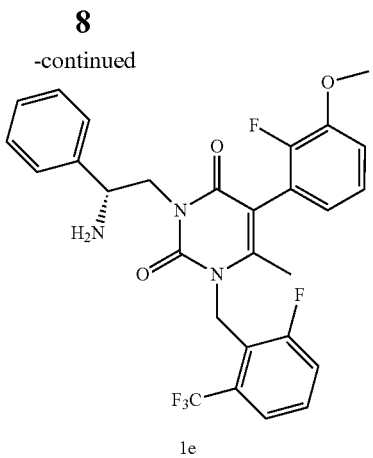

1e

Step 1A: 1-(2-Fluoro-6-trifluoromethyl-benzyl-6-methyl-1H-pyrimidine-2,4-dione (2-Fluoro-6-trifluoromethyl-benzyl)-urea (2.568 g, 10.9 mmol) in toluene (125 mL) was heated briefly to reflux under a Dean-Stark trap. T-butyl acetoacetate (5.0 g) was added and the mixture heated to reflux for 4 hrs. p-Toluenesulfonic acid monohydrate (2.82 g, 14.8 mmol) was added and the reflux was continued for one additional hour. Toluene was displaced with i-PrOH and the volume of the solution was reduced to approximately 30 mL. The solution was stirred overnight at room temp. The crystalline product was filtered and washed with a few mL of i-PrOH to provide 2.01 g (63% yield) of 1-(2-fluoro-6-trifluoromethyl-benzyl)-6-methyl-1H-pyrimidine-2,4-dione. LCMS (ESI) m/z 303.0 (MH+)

Step 1B: 1-(2-Fluoro-6-trifluoromethyl-benzyl)-5-iodo-6-methyl-1H-pyrimidine-2,4-dione To a 250 mL three-neck round bottom flask was charged 1-(2-fluoro-6-trifluoromethyl-benzyl)-6-methyl-1H-pyrimidine-2,4-dione 1a (25.0 g) and methanol (250 mL). Iodine monochloride (30.9 g) was charged over 2.5 min. The mixture was heated at 50° C. for 3 hours. After cooling to ambient temperature, the mixture was filtered. The cake was re-slurried in methanol (250 mL) and heated to 50° C. for 3 hours. After cooling to ambient temperature, the mixture was filtered and the filter cake was washed with methanol (50 mL). The off-white solid was dried in a vacuum oven at 50° C. to provide 1-(2-fluoro-6-trifluoromethyl-benzyl)-5-iodo-6-methyl-1H-pyrimidine-2,4-dione 1b (32.5 g, 90% yield). LCMS (ESI) m/z 429.3 (MH+). The material may be re-slurried in MeOH as needed.

Step 1C: 5-(2-Fluoro-3-methoxy-phenyl)-1-(2-fluoro-6-trifluoromethyl-benzyl)-6-methyl-1H-pyrimidine-2,4-dione To a reactor was charged 1-(2-fluoro-6-trifluoromethyl-benzyl)-5-iodo-6-methyl-1H-pyrimidine-2,4-dione 1b (20.0 kg), 2-fluoro-3-methoxyphenylboronic acid (8.7 kg), and acetone (60 L). The mixture was agitated and cooled to 15° C. and a potassium hydroxide/water solution (10.8 kg/64 L) was charged. The reactor contents were degassed for 30 min, then tri-t-butylphosphonium tetrafluoroborate (142 g) was added to the reactor and the contents mixed at 45° C. for 20 min. Palladium (II) acetate (52 g) was charged to the reactor and the contents were mixed at 55° C. The reaction mixture was stirred until the reaction was complete. Acetic acid (5.6 kg) was charged to the reactor over 1 hr, then the mixture was stirred at 55° C. for 30 min. The reactor contents were cooled to 25° C. over 2 hr. The solid was collected by centrifugation and the cake washed with water (40 L) followed by methanol (80 L). The solid was dried in a vacuum oven at 50° C. until the loss-on-drying was less than 1% to provide 5-(2-fluoro-3-methoxy-phenyl)-1-(2-fluoro-6-trifluoromethyl-benzyl)-6-methyl-1H-pyrimidine-2,4-dione 1c (16.6 kg, 83% molar yield) as an off-white solid. LCMS (ESI) m/z 427.1 (MH+).

Alternate Step 1C: 5-(2-Fluoro-3-methoxy-phenyl)-1-(2-fluoro-6-trifluoromethyl-benzyl)-6-methyl-1H-pyrimidine-2,4-dione To a reactor was charged 1-(2-fluoro-6-trifluoromethyl-benzyl)-5-iodo-6-methyl-1H-pyrimidine-2,4-dione 1b (5.0 kg), 2-fluoro-3-methoxyphenylboronic acid (2.58 kg), and acetone (5.5 L). The mixture was agitated and a potassium hydroxide/water solution (2.658 kg/19.0 L) was charged. The reactor contents were degassed for 30-60 min, then the internal temperature was adjusted to 40° C. 1,1-(bis-di-t-butylphosphino)ferrocene palladium dichloride (11.4 g) was added to the reactor and the contents mixed with jacket temperature set to 45° C. until the reaction was complete (2.5 hr). The reaction mixture was cooled to 20-30° C. Celite (1.25 kg) was charged to the reactor and stirred for more than one hour and the mixture was filtered through a Celite pad (0.51 kg). The reactor and Celite cake were washed with acetone/water/KOH (2.6 L/7.5 L/0.38 kg). The filtered solutions were passed through a line filter and added over a period of 1-1.5 hr to a mixture of THF/AcOH/Water (15.0 L/7.53 L/5.0 L) maintained at 62° C. The reactor contents were cooled to 20° C. over 2-3 hr. The mixture was filtered and the cake washed with 60:40 water/MeOH (2×12.6 L) followed by methanol (2×16 L). The solid was dried in a vacuum oven at 65° C. for 18 hr to provide 5-(2-fluoro-3-methoxy-phenyl)-1-(2-fluoro-6-trifluoromethyl-benzyl)-6-methyl-1H-pyrimidine-2,4-dione 1c (4.312 kg, 87% molar yield) as an off-white solid. LCMS (ESI) m/z 427.1 (MH+). If necessary, the material may be solubilized, re-treated with Celite, and crystallized as above to increase purity.

Step 1D: Methanesulfonic acid (S)-3-tert-butoxycarbonylamino-3-phenyl-propyl ester N-Boc-D-phenylglycinol (17.5 kg), diisopropylethylamine (11.4 kg), and tetrahydrofuran (79 L) were charged to a reactor, agitated, and the mixture was cooled to 0° C. Methanesulfonyl chloride (9.3 kg) was charged while maintaining the temperature below 10° C. Addition lines were rinsed with 26 L THF. After completion of the reaction, an aqueous 0.5 N HCl solution (3.6 kg conc. HCl/67 L water) was charged to the reactor while maintaining temperature below 10° C. After mixing, agitation was stopped and the layers were allowed to separate. The aqueous layer was discarded and heptane (175 L) was charged and the reactor contents were stirred at 0° C. for 1 hour. The mixture was filtered and the cake was washed with heptane (25 L) and dried at 40° C. under vacuum to provide methanesulfonic acid (S)-3-tert-butoxycarbonyl-amino-3-phenyl-propyl ester 1d (21.8 kg, 94% molar yield) as a white solid. LCMS (ESI) m/z 216.0 (M-100(Boc)H+)

Alternate Step 1D: Methanesulfonic acid (S)-3-tert-butoxycarbonylamino-3-phenyl-propyl ester N-Boc-D-phenylglycinol (5.0 kg), triethylamine (3.55 L), and dimethylformamaide (10.54 L) were charged to a reactor, agitated, and the mixture was cooled to 0° C. Methanesulfonyl chloride (1.79 L) was charged through a dip-tube while maintaining the temperature below 5° C. After completion of the reaction, acetone (15.0 L) was charged to the reactor while maintaining temperature below 5° C. Water (12.0 L) was charged to the mixture over 3 hr, maintaining temperature below 5° C., during which time crystallization occurred. An additional portion of water (18 L) was added while maintaining the temperature below 5° C. The mixture was filtered and the cake was washed with 2:1 (v/v) water:acetone three times (2×10 L, 1×6600 L) and dried between 25-40° C. under vacuum to provide methanesulfonic acid (S)-3-tert-butoxycarbonyl-amino-3-phenyl-propyl ester 1d (6.278 kg, 94.5% molar yield) as a white solid. LCMS (ESI) m/z 216.0 (M-100(Boc)H+)

Step 1E: 3-((R)-2-Amino-2-phenyl-ethyl)-5-(2-fluoro-3-methoxy-phenyl)-1-(2-fluoro-6-trifluoromethyl-benzyl)-6-methyl-1H-pyrimidine-2,4-dione Methanesulfonic acid (S)-3-tert-butoxycarbonylamino-3-phenyl-propyl ester 1d (19.7 kg), 5-(2-fluoro-3-methoxy-phenyl)-1-(2-fluoro-6-trifluoromethyl-benzyl)-6-methyl-1H-pyrimidine-2,4-dione 1c (16.5 kg), potassium carbonate (powder, 325 mesh, 13.4 kg) and DMF (101 L) were charged to a reactor. The mixture was stirred at 55° C. After reaction completion, the reactor was cooled to 20° C. and isopropyl acetate (132 L) was charged, followed by water (157 L). After agitation and settling, the layers were separated and the organic layer washed with water (87 L). After agitation and settling, the water layer was removed. To the organic layer was charged methanesulfonic acid (11.2 kg) and the reactor contents were heated to 60° C. for 1-2 hours. The reactor contents were cooled to 20° C. and a solution of potassium carbonate/water (26.8 kg/140 L) was added slowly, agitated, and then allowed to settle prior to separation of layers. The organic layer was treated with a solution of 85% phosphoric acid/H$_2$O (22.6 kg/236 kg). The mixture was agitated, allowed to settle, and the layers were separated. The aqueous layer was washed with isopropyl acetate (2×167 kg) and the layers were separated. A solution of potassium carbonate/water (36.1 kg/139 kg) was added slowly to the aqueous layer. Isopropyl acetate (206 kg) was charged; the mixture was agitated and then allowed to settle. The aqueous layer was removed and the organic layer was concentrated to provide a solution of 3-((R)-2-amino-2-phenyl-ethyl)-5-(2-fluoro-3-methoxy-phenyl)-1-(2-fluoro-6-trifluoromethyl-benzyl)-6-methyl-1H-pyrimidine-2,4-dione 1e in isopropyl acetate (125.4 kg, 30.7 kg contained, 86% yield) for use in the next step. LCMS (ESI) m/z 546.2 (MH+)

Alternate Step 1E: 3-((R)-2-Amino-2-phenylethyl)-5-(2-fluoro-3-methoxy-phenyl)-1-(2-fluoro-6-trifluoromethyl-benzyl)-6-methyl-1H-pyrimidine-2,4-dione Methanesulfonic acid (S)-3-tert-butoxycarbonylamino-3-phenyl-propyl ester 1d (177.54 g), 5-(2-fluoro-3-methoxy-phenyl)-1-(2-fluoro-6-trifluoromethyl-benzyl)-6-methyl-1H-pyrimidine-2,4-dione 1c (160.0 g), 1,1,3,3-tetramethylguanidine (117.72 mL) and DMF (320 mL) were charged to a reactor. The mixture was stirred at 40° C. After reaction completion (48 hr), 85% H₃PO₄/water (129.8 g/960 mL) was added followed by isopropyl acetate (960 mL). After agitation and settling, the layers were separated and the organic layer washed with 85% H₃PO₄/water (43.27 g/48 mL). After agitation and settling, the aqueous layer was removed and the organic layer washed with water (480 mL). After agitation and settling, the aqueous layer was removed. To the organic layer was charged water (76 mL) and methanesulfonic acid (108.2 g) and the reactor contents were heated to 60° C. for 6 hours. The reactor contents were cooled to 40° C. and a solution of potassium carbonate/water (259.34 g/1360 mL) was added slowly, agitated, and then allowed to settle prior to separation of layers. The organic layer was treated with a solution of 85% phosphoric acid/H₂O (129.81 g/1360 mL). The mixture was agitated, allowed to settle, and the layers were separated. The aqueous layer was washed with isopropyl acetate (2×1120 mL) and the layers were separated. A solution of potassium carbonate/water (259.34 g/480 mL) was added slowly to the aqueous layer. Isopropyl acetate (1360 mL) was charged; the mixture was agitated and then allowed to settle. The aqueous layer was removed and the organic layer was washed with water (480 mL) and the layers were separated. The organic later was filtered through a medium glass frit and the lines/filter were rinsed with 220 mL i-PrOAc. The organic layer was concentrated by distillation to approximately 550-750 mL volume. This solution was heated at 80° C. and heptane (640 mL) was added over one hour. NBI-54048 crystalline seeds (2.0 g) were charged after approximately one third of the heptane charge was complete. After heptane addition the mixture was maintained at 80° C. for 2 hr, then cooled to 10° C. over 180 min. The mixture was filtered to provide a solid that was dried under vacuum at 50-60° C. overnight. 3-((R)-2-amino-2-phenyl-ethyl)-5-(2-fluoro-3-methoxy-phenyl)-1-(2-fluoro-6-trifluoromethyl-benzyl)-6-methyl-1H-pyrimidine-2,4-dione 1e (170.9 g, 84% yield) was obtained as a white solid. LCMS (ESI) m/z 546.2 (MH+)

Example 2

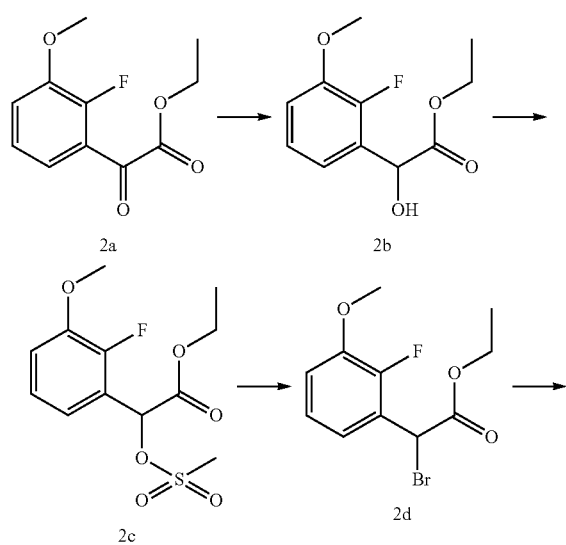

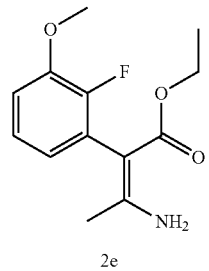

Step 2A: Ethyl-2-(2'-fluoro-3'-methoxyphenyl)-glyoxylate

N,N,N',N',N''-Pentamethyldiethylenetriamine (PMDFT, 36.0 g, 43.5 mL, 208 mmol) and anhydrous tetrahydrofuran (THF, 150 mL) were charged into a 3-necked 1 L round bottom flask purged with N₂. The solution was chilled to −78° C. with acetone—dry ice. Under continuous agitation and N₂ purge butyllithium (Bu-Li, 1.6 M solution in hexanes, 130 mL, 208 mmol) was added to the solution. Over a period of 30-45 min. 2-fluoroanisol (13.1 g, 11.7 mL, 104 mmol) diluted with anhydrous THF (50 mL) was added to the Bu-Li solution. One hour after the addition of 2-fluoroanisol the reaction mixture was slowly transferred to another 3-necked 1 L round bottom flask containing diethyloxalate (100 mL, 107.6 g, 736 mmol) diluted with anhydrous THF (100 mL) at −78° C. under N₂ purge. Agitation, −78° C. temp. and N₂ purge were maintained during the transfer and for one hour after. 85% H₃PO₄ (85 mL) diluted with water (240 mL) was added and the temperature was allowed to increase to room temp. The layers were separated and the aqueous phase was extracted with toluene (400 mL). The organic phases were combined and extracted with portions of water until the aqueous phase was neutral. The organic phase was evaporated in vacuo to yield an oily residue 2a (~102 g).

Step 2B: Ethyl-2-fluoro-3-methoxymandelate

The major portion of the crude 2a (90 g) from step 2A was dissolved in MeOH (180 mL) and AcOH (30 mL). Under continuous agitation at room temperature, NaBH₄ (9.5 g, 251 mmol) dissolved in DMF (95 mL) was slowly added. After completion of the reduction the solvents were removed by means of vacuum distillation (e.g. water bath temp. up to 85° C. at 25 mbar vacuum). The residue was partitioned between water (85 mL) and Et₂O (240 mL). The organic phase was washed with water (3×90 mL). The aqueous phases were extracted again first with Et₂O (250 mL) then with EtOAc (210 mL) in a "counter current" fashion. The extracts were concentrated down to oily residues 2b. The distribution of the product in various extracts is as follows:

| | |
|---|---|
| 1ˢᵗ Et₂O extract: | 18.35 g, purity: 81.2%* |
| 2ⁿᵈ Et₂O extract: | 2.39 g, purity: 100%* |
| EtOAc extract: | 0.68 g, purity: 65.8%* |

*The "purity" figures are based on the second Et₂O extract as 100%.

Step 2C: Ethyl-2-(2'-fluoro-3'-methoxyphenyl)-2-O-mesyl-glycolate

The crude oily concentrates of the ether extracts of 2b (20.7 g) were dissolved in a mixture of MeCN (60 mL) and Et₃N (40 mL). Under continuous stirring at room temperature, methanesulfonyl chloride (16.7 mL, 24.7 g, 216 mmol) diluted with MeCN (10 mL) was slowly added to the solution. At the end of the reaction the sample was partitioned between water (130 mL) containing Na₂CO₃ (1.5 g) and Et₂O (315 mL). The aqueous phase was extracted again with Et₂O (100 mL). The organic phases were combined and evaporated to an oil 2c (24.1 g).

Step 2D: Ethyl-2-bromo-(2'-fluoro-3'-methoxyphenyl)-acetate

The mesyl ester 2c (24.1 g) was dissolved in MeCN (50.0 mL). Crystalline Et₄N⁺.Br (15.2 g, 72.3 mmol) was added to the solution and the mixture was stirred at room temperature. The conversion was ca. 93% complete in five hours and 100% in four days. The mixture was concentrated to 45-50 mL and water (50 mL) was added. The resulting two-phase system was vigorously stirred while loaded onto a Mitsubishi SP207 (brominated cross-linked polystyrene) column (300 mL, 23 cm high). The column was eluted in a stepwise gradient manner with mixtures of water/MeCN in the following ratios: 70:30 (500 mL)-60:40-50:50-40:60-35:65-30:70-25:75 (250 mL each)—20:80 (500 mL)-15:85 and 10:90 (250 mL each). The fractions were evaluated by TLC first and the fractions containing the product were assayed by HPLC. Like fractions were combined and the organic component was removed by distillation in vacuo. The oily phases under the aqueous residues were extracted with CH₂Cl₂. The organic phases were dried to yield 2d as a yellow oil. The yield was calculated as 11.45 g from assays based on the best fraction available being used as a standard.

Step 2E: Ethyl-2-(2'-fluoro-3'-methoxyphenyl)-3-aminocrotonate

A sample of bromoacetate 2d (3.48 g, ca. 86% pure based on the purest sample available as standard, 10.3 mmol) was dissolved in HPLC grade MeCN (10.0 mL). The resulting solution was evaporated to an oily residue in a stream of N₂ at elevated temperature (drying block set at 60° C.). Simultaneously, Zn powder (−100 mesh, 0.714 mg, 10.9 mmol) was suspended in HPLC grade MeCN (5.0 mL) and was completely dried under the same conditions as above. All reactants were cooled to room temp. While kept in a strictly inert atmosphere, 2d sample was re-dissolved in anhydrous MeCN (10.0 mL) and transferred to the vial containing Zn powder. Under vigorous agitation the reaction was initiated within the time interval of 0-10 min. and was complete in 45-60 min. The reaction mixture was centrifuged to remove excess Zn powder. The supernatant was partitioned between toluene (100 mL) and water (70 mL)—AcOH (4.0 mL). The organic phase was washed with water (70 mL) and water (70 mL)—conc. NH₄OH (2.0 mL). The organic phase was washed again with water (2×70 mL) and evaporated to an oil 2e (3.99 g, ~69% pure). LCMS (ESI) m/z 254.5 (MH+)

Example 3

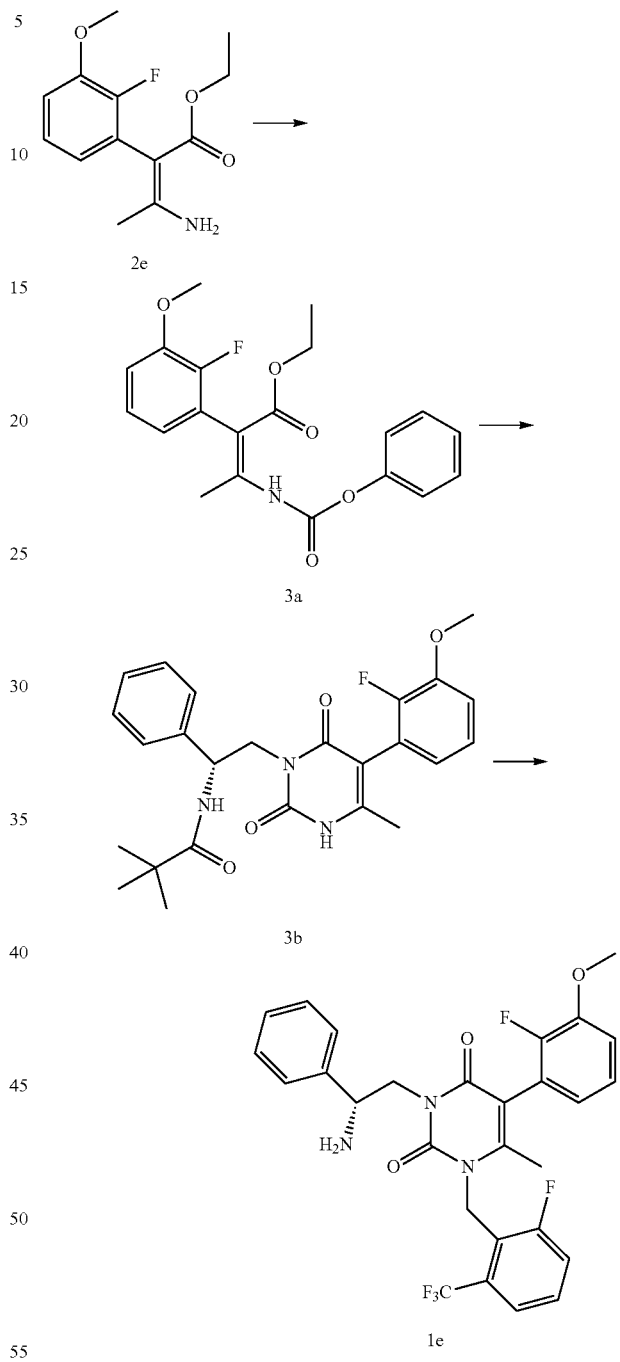

Step 3A: (Z)-2-(2-Fluoro-3-methoxy-phenyl)-3-phenoxycarbonylamino-but-2-enoic acid ethyl ester Aminocrotonate 2e (5.0 g, 19.7 mmol), toluene (50 mL), calcium oxide (powdered, 2.5 g, 44.6 mmol), and phenyl chloroformate (3.4 g, 21.67 mmol) were combined in a reactor. The slurry was stirred at 75° C. for 10 hours. The mixture was cooled to 25° C. and filtered through a #1 filter paper. The reactor and cake were washed with 50-100 mL of toluene. The toluene solutions were combined and stripped off under a 10 mm vacuum to give 7.5 g of carbamate residue 3a.

Step 3B: N—{(R)-2-[5-(2-Fluoro-3-methoxy-phenyl)-4-methyl-2,6-dioxo-3,6-dihydro-2H-pyrimidin-1-yl]-1-phenyl-ethyl}-2,2-dimethyl-propionamide DMF (anhydrous, 70 mL) was added to carbamate residue 3a (7.5 g, 19.7 mmol) and the mixture was cooled to 0° C. t-BOC-(1R)-amino-2-amino-1-phenylethane acetate salt (6.41 g, 21.6 mmol) was added followed by K$_2$CO$_3$ (4.08 g, 29.6 mmol). The mixture was stirred for ~3 hours (all carbamate 3a (t$_R$=11.5 minute in HPLC method 1) was converted to urea intermediate (t$_R$=10.5 minute in HPLC method 1)). The temperature was raised to 60° C. to control the CO$_2$ release. The mixture was heated for 2-3 hours then 210 mL of water was slowly added over 30-60 minutes maintaining the temperature at 60° C. The slurry was stirred for 30-60 minutes at 50-60° C. and was cooled down to 25° C. over 30-60 minutes. The slurry was filtered and the cake was washed with 210 mL water to remove the residual base. The cake was dried at 10 mm/50° C. to give 6.5 g (70% yield) of off-white fine needle crystal 3b. Alternately, the cake may be washed with acetonitrile/water 2:1 before drying.

Step 3C: 3-((R)-2-Amino-2-phenyl-ethyl)-5-(2-fluoro-3-methoxy-phenyl)-1-(2-fluoro-6-trifluoromethyl-benzyl)-6-methyl-1H-pyrimidine-2,4-dione Uracil 3b (14.5 g, 30.9 mmol), sodium carbonate (50.0 g, 106 mmol), sodium bromide (25.0 g, 102.9 mmol), anhydrous DMF (200 mL), and 2-flouro-6-trifluoromethylbenzyl bromide (12.0 g, 46.7 mmol) in 50 mL toluene were heated at 70-90° C. for 10 hours (HPLC showed all of the 3b was consumed). The mixture was cooled to room temperature and was slowly charged with 170 mL of conc. HCl solution. (Optionally, the solid carbonate and sodium bromide can be filtered off before the addition of the HCl resulting in the use of less HCL solution). The solution was heated at 60° C. for 10 hours. The pH of the solution was adjusted to 7-8 by slowly adding solid sodium carbonate. 600 mL of DI water was added and the solution was extracted with 2×250 mL isopropyl acetate. The phases were separated and the organic layer was washed with 2×100 mL of DI water. The organic layer was concentrated to 150 mL and was extracted with 150 mL 10% phosphoric acid. The aqueous layer was agitated with 450 mL of isopropyl acetate and the mixture was neutralized with saturated sodium bicarbonate solution to pH 7. The phases were separated and the organic layer was washed with 2×100 mL of water then dried over anhydrous sodium sulfate. The organic layer was filtered and the filtrate was concentrated at 10 mm and 50-60° C. to give 15.8 g of 1e as sticky oil with >98% HPLC peak are at 254 um (t$_R$=6.61 min, HPLC method 1). The yield was 91%. The oil can be triturated with hexane to further remove some of the impurities.

Example 4

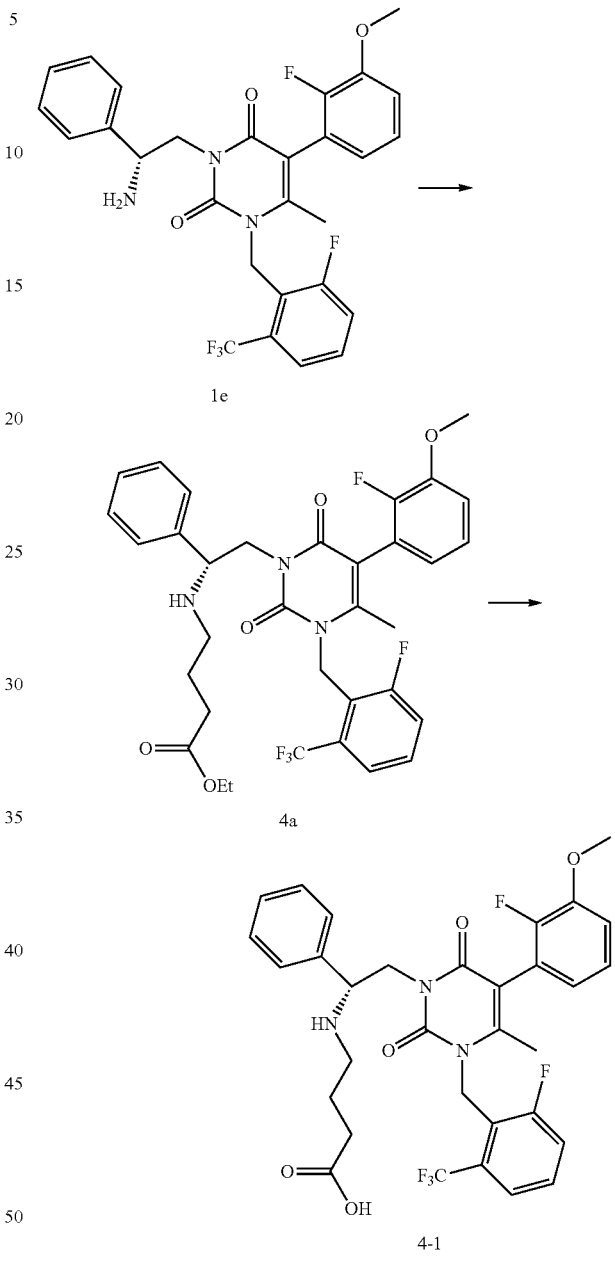

Step 4A: 4-((R)-2-[5-(2-Fluoro-3-methoxy-phenyl)-3-(2-fluoro-6-trifluoromethyl-benzyl)-4-methyl-2,6-dioxo-3, 6-dihydro-2H-pyrimidin-1-yl]-1-phenyl-ethylamino)-butyric acid ethyl ester To a reactor was charged a solution of 3-((R)-2-amino-2-phenyl-ethyl)-5-(2-fluoro-3-methoxy-phenyl)-1-(2-fluoro-6-trifluoromethyl-benzyl)-6-methyl-1H-pyrimidine-2,4-dione 1e in isopropyl acetate (30.7 kg in 125.4 kg solution). Dimethylformamide (28.8 kg) was charged and the mixture was distilled under vacuum to remove the isopropyl acetate. Ethyl-4-bromobutyrate (11.8 kg) was charged to the reactor followed by diisopropylethylamine (8.87 kg). The reactor contents were heated to 52° C. and stirred until completion of reaction. The reactor was cooled to 22° C. and isopropyl acetate (144 kg) and water (144 kg) were added. The mixture was agitated and the layers allowed to settle. The water layer was removed and the organic layer was washed with water (144 kg). The organic layer was treated with a solution of 85% phosphoric acid/$H_2O$ (15.6 kg/173 kg). The mixture was agitated, allowed to settle, and the layers were separated. The organic layer was treated with a solution of 85% phosphoric acid/$H_2O$ (4.03 kg/28.8 kg). The mixture was agitated, allowed to settle, and the layers were separated. The aqueous phosphate layers were combined and washed with isopropyl acetate (28.8 kg). After layer separation, isopropyl acetate (144 kg) was added to the aqueous layer, followed by slow addition of a solution of potassium carbonate/water (35.1 kg/43.2 kg) while mixing. The layers were separated and the organic layer was concentrated by vacuum distillation. The solution was passed through a silica gel plug pre-conditioned with $CH_2Cl_2$ and the plug eluted using i-PrOAc/$CH_2Cl_2$ (31 kg/190 kg) in four portions. Appropriate portions were combined and the solution was concentrated initially by atmospheric pressure distillation followed by vacuum distillation. The concentrated solution of 4-((R)-2-[5-(2-fluoro-3-methoxy-phenyl)-3-(2-fluoro-6-trifluoromethyl-benzyl)-4-methyl-2, 6-dioxo-3, 6-dihydro-2H-pyrimidin-1-yl]-1-phenyl-ethylamino)-butyric acid ethyl ester 4a (86.4 kg total, ~29.8 kg of 4a, 80% yield) was used in the next step. LCMS (ESI) m/z 660.2 (MH+)

Step 4B: 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid To a reactor was charged a solution of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid ethyl ester 4a (86.4 kg solution, containing ~29.8 kg of 4a). The solution was concentrated by vacuum distillation, followed by addition of ethanol (59.6 kg). The solution was concentrated by vacuum distillation. After distillation was complete, ethanol (59.6 kg) was charged to the reactor, followed by a solution of NaOH/water (4.47 kg/59.6 kg). The reactor contents were heated at 35° C. for two hours until reaction completion. The reactor contents were concentrated using vacuum distillation, water (89.4 kg) was added, and the reactor contents were concentrated using vacuum distillation. Water (149 kg) was added and the solution was cooled to 10-15° C. A solution of conc. HCl/water (8.05 kg/29.8 kg) was added slowly over ~1 hr while maintaining the temperature between 10-15° C. until the pH was 6.1. The slurry was stirred at 22° C. for 16 hours and filtered. The reactor and filter cake were washed with water (2×50 kg) and the solid product was dried under vacuum at 37° C. to provide 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid 4-1 as an off-white solid (26.1 kg, 91% yield). LCMS (ESI) m/z 632.2 (MH+)

Example 5

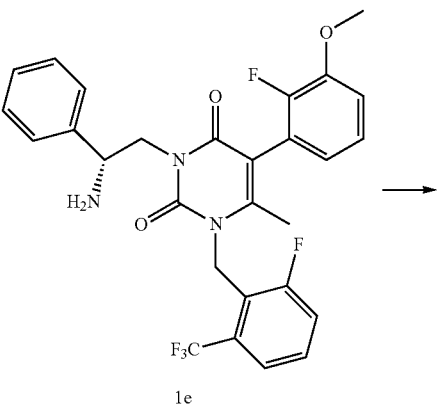

1e

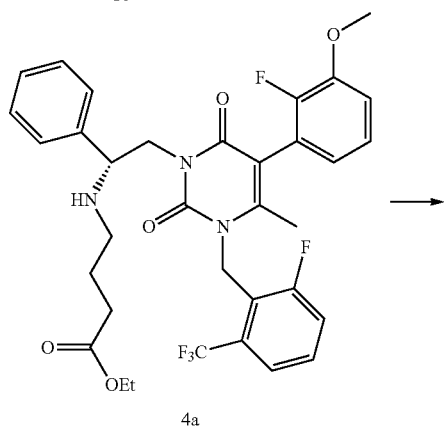

4a

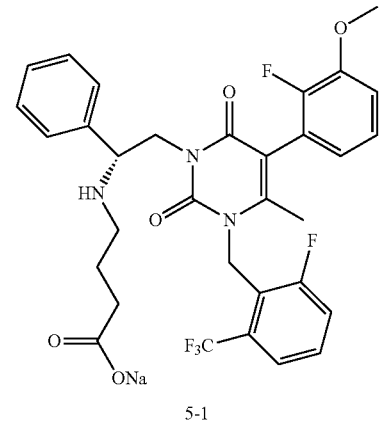

5-1

Step 5A: 4-((R)-2-[5-(2-Fluoro-3-methoxy-phenyl)-3-(2-fluoro-6-trifluoromethyl-benzyl)-4-methyl-2, 6-dioxo-3, 6-dihydro-2H-pyrimidin-1-yl]-1-phenyl-ethylamino)-butyric acid ethyl ester To a reactor was charged a solution of 3-((R)-2-amino-2-phenyl-ethyl)-5-(2-fluoro-3-methoxy-phenyl)-1-(2-fluoro-6-trifluoromethyl-benzyl)-6-methyl-1H-pyrimidine-2,4-dione 1e in isopropyl acetate (19.0 kg in 59.6 L solution). Dimethylformamide (18 L) was charged and the mixture was distilled under vacuum to remove the isopropyl acetate. Ethyl-4-bromobutyrate (7.83 kg) was charged to the reactor followed by diisopropylethylamine (5.87 kg). The reactor contents were heated to 55° C. and stirred until completion of reaction. The reactor was cooled to 20° C. and isopropyl acetate (110 L) and water (96 L) were added. The mixture was agitated and the layers allowed to settle. The water layer was removed and the organic layer was washed with water (95 L). The organic layer was treated with a solution of 85% phosphoric acid/H$_2$O (10.4 kg/152 L). The mixture was agitated, allowed to settle, and the layers were separated. The organic layer was treated with a solution of 85% phosphoric acid/H$_2$O (2.7 kg/19 L). The mixture was agitated, allowed to settle, and the layers were separated. The aqueous phosphate layers were combined and washed with isopropyl acetate (21 L). After layer separation, dichloromethane (109 L) was added to the aqueous layer, followed by slow addition of a solution of potassium carbonate/water (23.2 kg/29 L) while mixing. The layers were separated and the organic layer was concentrated by vacuum distillation. The solution was passed through a silica gel plug preconditioned with CH$_2$Cl$_2$ and the plug eluted using EtOH/CH$_2$Cl$_2$ (5 L/469 L). Appropriate portions were combined and the solution was concentrated by vacuum distillation. Ethanol (80 L) was charged to provide a concentrated stock solution of 4-((R)-2-[5-(2-fluoro-3-methoxy-phenyl)-3-(2-fluoro-6-trifluoromethyl-benzyl)-4-methyl-2, 6-dioxo-3, 6-dihydro-2H-pyrimidin-1-yl]-1-phenyl-ethylamino)-butyric acid ethyl ester 4a (82.9 kg total, ~17.3 kg of 4a, 75% yield) that was used in the next step. LCMS (ESI) m/z 660.2 (MH+)

Alternate Step 5A: 4-((R)-2-[5-(2-Fluoro-3-methoxy-phenyl)-3-(2-fluoro-6-trifluoromethyl-benzyl)-4-methyl-2, 6-dioxo-3, 6-dihydro-2H-pyrimidin-1-yl]-1-phenyl-ethylamino)-butyric acid ethyl ester To a reactor was charged a solution of 3-((R)-2-amino-2-phenyl-ethyl)-5-(2-fluoro-3-methoxy-phenyl)-1-(2-fluoro-6-trifluoromethyl-benzyl)-6-methyl-1H-pyrimidine-2,4-dione 1e (3000 g) and dimethylformamide (4.5 L). The mixture was stirred and diisopropylethylamine (924 g) and ethyl-4-bromobutyrate (1287 g) were charged to the reactor and the reactor contents were heated to 80-85° C. After completion of the reaction (4 hr) the contents were cooled to 25-30° C. and isopropyl acetate (15.0 L) and water (9.0 L) were added. The mixture was agitated and the layers allowed to settle. The water layer was removed and the organic layer was washed with citric acid/water (300 g/6.0 L). The layers were separated and the organic layer was treated with a solution of 85% phosphoric acid/H$_2$O (1055 g/21.0 L). The mixture was agitated, allowed to settle, and the layers were separated. The organic layer was treated with a solution of 85% phosphoric acid/H$_2$O (422 g/6.0 L). The mixture was agitated, allowed to settle, and the layers were separated. The aqueous phosphate layers were combined and washed with isopropyl acetate (2×6.0 L). After layer separation, isopropyl acetate (15.0 L) was added to the aqueous layer, followed by slow addition of a solution of potassium carbonate/water (3.04 kg/4.5 L) while mixing. The layers were separated and the aqueous layer was extracted with i-PrOAc (6.0 L). After layer separation, the combined organic layers were washed with sodium bicarbonate/water (1.20 kg/15.0 L). Reagent alcohol (6.0 L) was added to the organic layer and the solution concentrated by vacuum distillation until the reactor volume was ~9.0 L. Reagent alcohol (12.0 L) was added and distillation was resumed until the volume was ~9.0 L. The concentrated solution of 4-((R)-2-[5-(2-fluoro-3-methoxy-phenyl)-3-(2-fluoro-6-trifluoromethyl-benzyl)-4-methyl-2, 6-dioxo-3, 6-dihydro-2H-pyrimidin-1-yl]-1-phenyl-ethylamino)-butyric acid ethyl ester 4a was used in the next step. LCMS (ESI) m/z 660.2 (MH+)

Step 5B: 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid sodium salt To a reactor was charged a stock solution of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid ethyl ester 4a (81.8 kg solution, containing ~17.1 kg of 4a). A solution of NaOH/water (2.2 kg/70 L) was added and the reactor contents were stirred at 20-25° C. for five hours until reaction completion. The reactor contents were concentrated using vacuum distillation. Water (124 L) was added and the solution was passed through a 5 km line filter. Methyl isobutyl ketone (120 L) was charged and the mixture heated to 55° C. Separate the layers and add methyl isobutyl ketone (120 L) to the aqueous layer at ambient temperature. Agitate the mixture and add 48% aqueous sodium hydroxide (33 kg). Separate the layers and wash the aqueous layer with methyl isobutyl ketone (51 L). Separate the layers and wash the combined methyl isobutyl ketone layers with an aqueous brine solution (15.4 kg NaCl/44 L water). Separate the layers and concentrate the organic layer to ~2-3 volumes methyl isobutyl ketone. Filter the concentrated solution through a 0.2 μm filter. Charge the methyl isobutyl ketone solution to a well-agitated reactor containing heptane (171 L) cooled to 20° C. The mixture is stirred for two hours, filtered, and the cake is washed with heptane (10 L) to provide 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid sodium salt 5-1 as an off-white solid (13.2 kg, 78% yield). LCMS (ESI) m/z 632.2 (MH+)

Alternate Step 5B: 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid sodium salt To a reactor was charged a solution of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid ethyl ester 4a from the previous step. Reagent alcohol (6.0 L) was added and the temperature adjusted to 20° C. A solution of NaOH/water (440 g/6.0 L) was added and the reactor contents were stirred at 20-25° C. for two hours until reaction completion. Water (9.0 L) was added and the reactor contents were concentrated using vacuum distillation to a volume of approximately 15.0 L. Water (15.0 L) and methyl isobutyl ketone (9.0 L) was charged, the mixture was agitated, the layers were separated, and the aqueous layer was retained. A second wash with methyl isobutyl ketone may be performed if needed. Methyl isobutyl ketone (9.0 L) was added and the mixture concentrated by vacuum distillation to a volume of approximately 30 L and ethanol content less than 3%. The reactor contents were set to a temperature of 25-30° C. and sodium chloride (4507 g) and methyl isobutyl ketone (21.0 L) were charged to the reactor and agitated. The layers were separated and the organic layer was concentrated to ~2-3 volumes methyl isobutyl ketone. The concentrated solution was filtered through Celite and a 0.3 μm line filter. The filtered solution was charged to a well-agitated reactor containing heptane (30.0 L) cooled to 10-20° C. The mixture was stirred for two hours, filtered, and the cake was washed with heptane (8 L). The product was dried in a vacuum oven for 24-48 hr at 70-75° C. to provide 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid sodium salt 5-1 as an off-white solid (2.46 kg, 64% yield). LCMS (ESI) m/z 632.2 (MH+)

cake for 1 h to provide 6.0 g (87%) of 4-((R)-2-[5-(2-Fluoro-3-methoxy-phenyl)-3-(2-fluoro-6-trifluoromethyl-benzyl)-4-methyl-2, 6-dioxo-3, 6-dihydro-2H-pyrimidin-1-yl]-1-phenyl-ethylamino)-butyric acid ethyl ester HCl salt 4a.HCl as a white solid, LCMS (ESI) m/z 660.2 (MH+ of free base). Elemental analysis: Cl, 5.21%

Example 6

Example 7

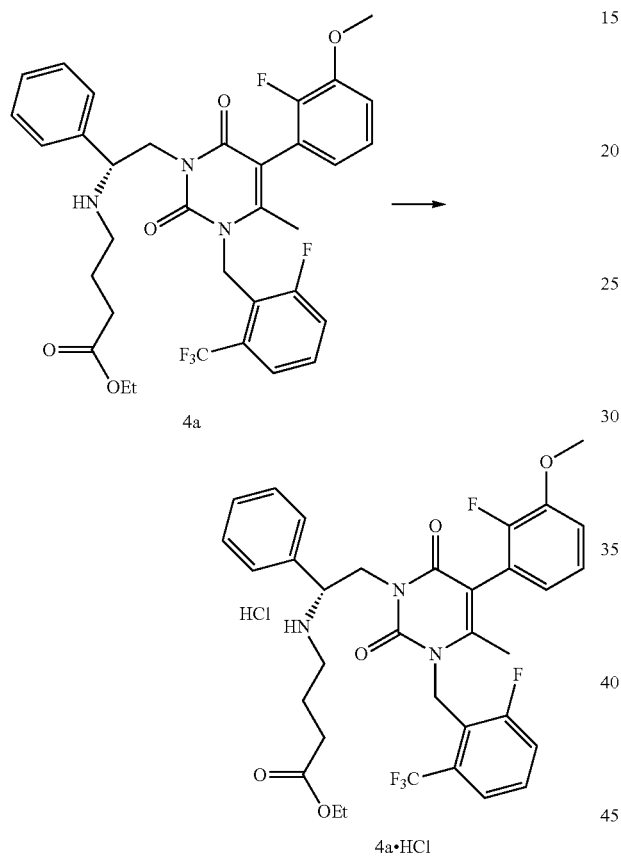

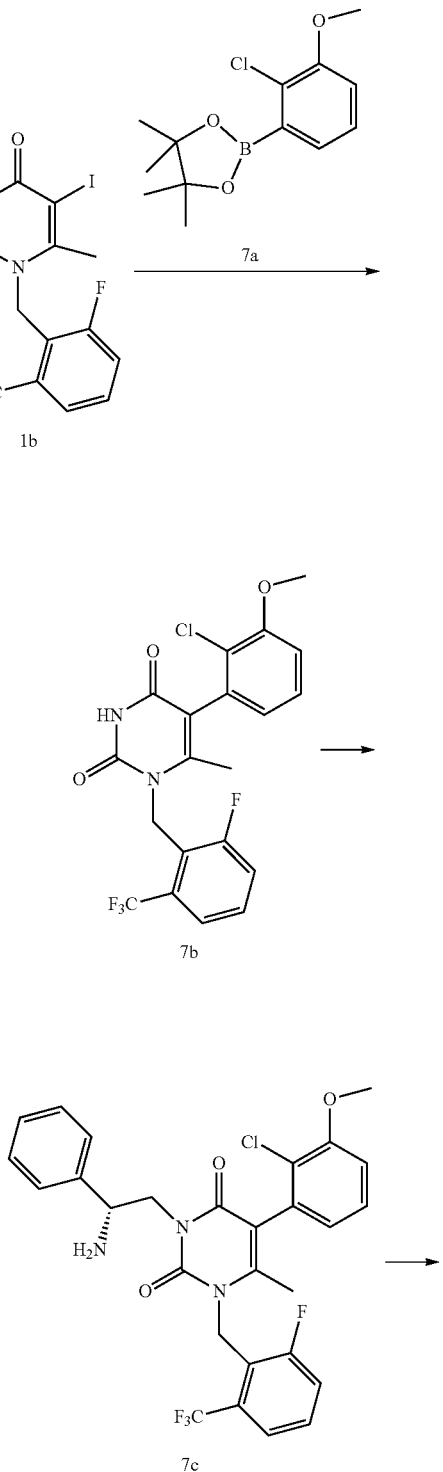

Step 6A

To a stock solution of 4-((R)-2-[5-(2-fluoro-3-methoxy-phenyl)-3-(2-fluoro-6-trifluoromethyl-benzyl)-4-methyl-2, 6-dioxo-3, 6-dihydro-2H-pyrimidin-1-yl]-1-phenyl-ethyl-amino)-butyric acid ethyl ester (6.55 g, 9.94 mmol) in i-PrOAc (140 mL) was added conc. HCl (12 N, 0.88 mL, 10.6 mmol) solution in water dropwise at room temperature over 2 min. Approximately 95 mL of water and i-PrOAc mixture was removed by distillation under reduced pressure. Isopropyl alcohol (1.28 mL) was added to provide a homogeneous solution at 28° C. The reaction mixture was added dropwise into a vigorously stirred solution of n-heptane (65 mL) at 5° C. A white precipitate was formed immediately and the mixture became thick upon completion of addition. The white slurry was stirred for 18 h at room temperature. The white solid was collected by pressure filtration under nitrogen and dried by passing nitrogen through the filter

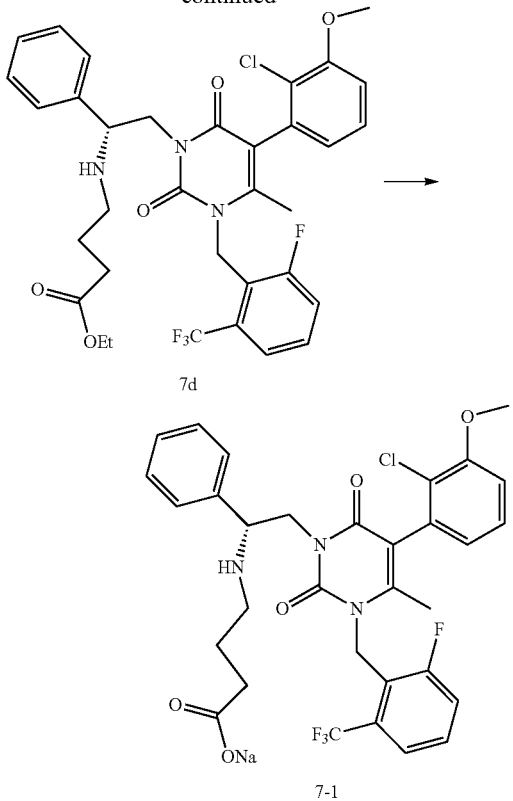

Step 7A: 2-(2-Chloro-3-methoxy-phenyl)-4,4,5,5-tetramethyl-[1,3,2]dioxaborolane

To a stirred solution of 2-chloro-3-(4,4,5,5-tetramethyl-[1,3,2]dioxaborolan-2-yl)-phenol (830 g, 3.26 mol) in dry DMF (4.15 L) was added potassium carbonate (1126.4 g, 8.15 mol) under an inert atmosphere. Me$_2$SO$_4$ (402 mL, 4.24 mol) was added slowly to control the resulting exotherm (addition over 30 minutes gave a temperature rise from 28° C. to 55° C.) and after complete addition the reaction was stirred for 10 minutes. The reaction mixture was added to stirring HCl (5.98 L, 2 N, aq.) very slowly to control effervescence and the resulting precipitate stirred for 2 hours. The solids were filtered and washed with water (1 L) and dried in a vacuum oven over drying agent for 4 days to give 2-(2-chloro-3-methoxy-phenyl)-4,4,5,5-tetramethyl-[1,3,2]dioxaborolane 7a as a white powder (746.7 g, 2.78 mol, 85%).

Step 7B: 5-(2-Chloro-3-methoxy-phenyl)-1-(2-fluoro-6-trifluoromethyl-benzyl)-6-methyl-1H-pyrimidine-2,4-dione Compound 1b (80 g, 0.19 mol), 7a (60.22 g, 0.22 mol), HP(t-Bu)$_3$BF$_4$ (13.01 g, 44.85 mmol), and Pd$_2$(dba)$_3$ (13.69 g, 14.95 mmol) were charged to the reaction vessel and purged with an inert atmosphere. Degassed THF (560 mL) was added followed by NaOH (31.45 g, 0.56 mol) in degassed water (128.8 mL) and the reaction warmed to 45° C. After 2 hours acetic acid (56 mL) was added and stirred for 15 minutes. After settling, the layers were separated and the organic layer was filtered through celite, rinsing with hot THF (2×160 mL). The filtrate was concentrated in vacuo to a slurry, to which was added N-acetyl cysteine (15.84 g) as a solution in water (160 mL) and ethanol (640 mL) and stirred for 2 hours at 75° C. under an inert atmosphere. The slurry was cooled to RT, and the solids filtered off, washed with ethanol:water (8:2, 2×160 mL) to give 5-(2-chloro-3-methoxy-phenyl)-1-(2-fluoro-6-methyl-benzyl)-6-methyl-1H-pyrimidine-2,4-dione 7b as a white solid (58.6 g, 0.13 mol, 70%).

Step 7C: 3-((R)-2-Amino-2-phenyl-ethyl)-5-(2-chloro-3-methoxy-phenyl-1-(2-fluoro-6-methyl-benzyl)-6-methyl-1H-perimidine-2,4-dione 7b (120 g, 0.271 mol), 1d (128.34 g, 0.407 mol) and K$_2$CO$_3$ (93.64 g, 0.407 mol) were charged to the reaction vessel under an inert atmosphere and suspended in DMF. The resulting slurry was warmed to 50° C. and stirred for 17 hours. The reaction was incomplete so additional 1d (50 g, 0.158 mol) and DMF (300 mL) were added. The reaction was complete after 32 hours and the mixture was cooled to RT. i-PrOAc (1 L) and water (1 L) were added and stirred for 30 minutes. The layers were separated and MeSO$_3$H (52.8 mL, 0.813 mol) was added slowly to the organic layer controlling the exotherm (24.4° C. to 41.0° C.). The mixture warmed to 60° C. and was stirred for 3 hours. The mixture was cooled to RT and was added slowly to a mixture of K$_2$CO$_3$ (186.99 g, 1.35 mol) in water (975 mL). After stirring for 15 minutes, the organic layer was separated and extracted with a H$_3$PO$_4$ solution (94 g of 85% H$_3$PO$_4$ in 975 mL water). The aqueous layer was slowly added to K$_2$CO$_3$ (186.99 g, 1.35 mol) in water (975 mL), followed by i-PrOAc (1100 mL). The mixture was stirred for 10 minutes and the layers separated. The i-PrOAc layer was dried (NaSO$_4$) and concentrated to give 3-((R)-2-amino-2-phenyl-ethyl)-5-(2-chloro-3-methoxy-phenyl)-1-(2-fluoro-6-methyl-benzyl)-6-methyl-1H-pyrimidine-2,4-dione 7c as a foaming solid (145.5 g, 0.25 mol, 95% crude yield, uncorrected for purity).

Step 7D: 4-((R)-2-[5-(2-chloro-3-methoxy-phenyl)-3-(2-fluoro-6-trifluoromethyl-benzyl)-4-methyl-2,6-dioxo-3, 6-dihydro-2H-pyrimidin-1-yl]-1-phenyl-ethylamino)-butyric acid ethyl ester 7c (145.5 g, 0.259 mol) was dissolved in DMF (146 mL) under an inert atmosphere. 4-Bromobutyrate (42.6 mL, 0.298 mol) was added followed by i-Pr$_2$EtN (58.65 mL, 0.337 mol) and was stirred overnight at 54° C. The mixture was cooled to RT and i-PrOAc (620 mL), water (620 mL) were added, and the mixture was stirred for 30 minutes. After separation, the organic layer was washed with water (620 mL) and extracted with a H$_3$PO$_4$ solution (67.3 g of 85% H$_3$PO$_4$ in 1 L water). The organic was extracted a second time with a H$_3$PO$_4$ solution (17.6 g of 85% H$_3$PO$_4$ in 126 mL water). The combined aqueous phosphate extracts were washed with i-PrOAc (130 mL). CH$_2$Cl$_2$ (950 mL) was added to the aqueous phosphate layer followed by a slow addition of a solution of K$_2$CO$_3$ (172 g, 1.24 mol) in water (188 mL). The mixture was stirred for 30 minutes and after separation the organic dried (NaSO$_4$) and concentrated in vacuo to give 4-((R)-2-[5-(2-chloro-3-methoxy-phenyl)-3-(2-fluoro-6-trifluoromethyl-benzyl)-4-methyl-2, 6-dioxo-3, 6-dihydro-2H-pyrimidin-1-yl]-1-phenyl-ethylamino)-butyric acid ethyl ester 7d as a foaming oil (121 g, 0.179 mol, 70%).

Step 7E: 4-((R)-2-[5-(2-chloro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid sodium salt NaOH (338 mL, 169 mmol, 0.5 M aq.) was added to a solution of 7d (103.9 g, 153.68 mol) in EtOH (472 mL) and the mixture was stirred for 2 hours. The EtOH was distilled off and water added to a total volume of 1080 mL (10.5 mL/g). This mixture was passed through a filter and washed with MIBK (600 mL×2). MIBK (700 mL) was added followed by NaOH (289 mL, 50% w/w) and extracted. The organic layer was separated and the aqueous extracted with MIBK (250 mL) and the combined organic layers washed with brine (500 mL), dried (NaSO$_4$) and concentrated in vacuo to give a foam. This was lyophilized from 300 mL water to give 4-((R)-2-[5-(2-chloro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid sodium salt 7-1 as an off white powder (92 g).

Example 8

Spray Drying Compound 5-1

Compound 5-1 was spray dried in a Buchi Mini Spray Dryer model B-290. In the B-290, compound 5-1 was dried co-currently with the drying gas flowing at approximately 30 m$^3$/hr. The B-290's spraying chamber was about 5.5 liters. Therefore, the B-290's average drying residence time was about 0.6 sec. Atomization was achieved by passing nitrogen gas and feed stream through a two fluid nozzle atomizer.

Several drying runs were conducted using different solvents and adjusting the pH. The following table shows the conditions of runs. All runs resulted in an amorphous solid with no change in impurity profile.

| Run # | Cmpd 5-1 (g) | Inlet temp (° C.) | Outlet temp (° C.) | Solvent |
|---|---|---|---|---|
| 1 | 2 | | | 8 v/w 50:50 EtOH:H$_2$O |
| 2 | 2 | 110 | 55 | 8 v/w H$_2$O |
| 3 | 2 | 110 | 64 | 8 v/w 60:40 H$_2$O:EtOH |
| 4 | 2 | 100 | 54 | 8 v/w 50:50 MeOH:H$_2$O |
| 5 | 2 | 70 | 49 | 8 v/w MeOH |
| 6 | 2 | 100 | 55 | 8 v/w 50:50 MeOH:H$_2$O, XS NaOH |
| 7 | 2 | 100 | 57 | 8 v/w 50:50 MeOH:H$_2$O |
| 8 | 4 | 110 | 65 | ~12 v/w 50:50 MeOH:H$_2$O |
| 9 | 4 | 110 | 59 | ~6 v/w 50:50 MeOH:H$_2$O, XS NaOH |

All trials run with N$_2$ flow of ~30 m$^3$/hr, atomization flow of 0.45 m$^3$/hr, and solution feed rate of approx. 5 mL/min Example 9

Formation of Solid Amorphous Mixtures of Compound 5-1 Using Solvent Evaporation

Appropriate amounts of compound 5-1 and polymer were dissolved by bath sonication in a solvent system comprising DCM/ethanol 1:1 (w/w), in a 250 mL Quickfit round bottomed flask. The solvent was then removed as rapidly as possible under vacuum. The vacuum was maintained until all obvious traces of the solvent had been removed, and was then transferred to a freeze drier chamber and left overnight at high vacuum. The dried material was removed from the flask using a spatula and analyzed for amorphous content using XRPD and DSC. Compound 5-1 was recovered as an amorphous solid mixture with polymer.

| Run # | Polymer:compound 5-1 ratio | Polymer |
|---|---|---|
| 1 | 3:1 | Kollidon 30 |
| 2 | 3:1 | Kollidon 90 F |
| 3 | 3:1 | HPMC |
| 4 | 3:1 | Kollidon 30 |
| 5 | 3:1 | Kollidon 90 F |
| 6 | 3:1 | HPMC |

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound of structure (VII)

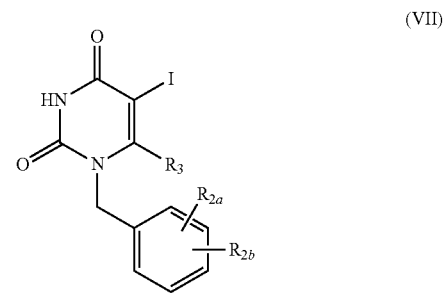

(VII)

wherein:
R$_{2a}$ and R$_{2b}$ are the same or different and independently halogen, trifluoromethyl, cyano or —SO$_2$CH$_3$; and
R$_3$ is hydrogen or methyl.

2. The compound of claim 1 wherein R$_{2a}$ is F and R$_{2b}$ is —CF$_3$.

3. The compound of claim 2 wherein R$_3$ is hydrogen.

4. A compound of structure (VII)

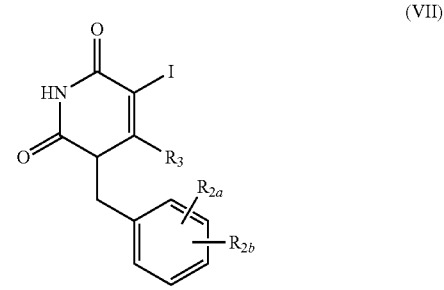

(VII)

wherein:
R$_{2a}$ and R$_{2b}$ are different and independently hydrogen, halogen, trifluoromethyl, cyano or —SO$_2$CH$_3$; and
R$_3$ is hydrogen or methyl.

5. The compound of claim 4 wherein R$_{2a}$ is F.
6. The compound of claim 5 wherein R$_3$ is methyl.
7. The compound of claim 4 wherein R$_{2b}$ is –CF$_3$.
8. The compound of claim 7 wherein R$_3$ is methyl.

* * * * *

UNITED STATES PATENT AND TRADEMARK OFFICE
CERTIFICATE OF CORRECTION

PATENT NO. : 10,494,347 B2
APPLICATION NO. : 15/833513
DATED : December 3, 2019
INVENTOR(S) : Donald J. Gallagher et al.

Page 1 of 1

It is certified that error appears in the above-identified patent and that said Letters Patent is hereby corrected as shown below:

On the Title Page

In Column 1, item (73), under Assignee, replace "Deigo," with --Diego,--

In Column 1, item (60), under "Related U.S. Application Data", Lines 7-8, replace "filed as application No. PCT/US2008/082873" with --which is a National Stage Entry of PCT/US2008/082873, filed--

In the Claims

In Column 26, Claim 4, Lines 45-55, replace " 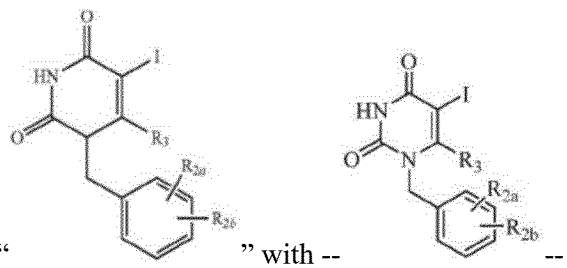 " with -- --

Signed and Sealed this
Fourteenth Day of September, 2021

Drew Hirshfeld
*Performing the Functions and Duties of the
Under Secretary of Commerce for Intellectual Property and
Director of the United States Patent and Trademark Office*